(12) United States Patent
Oldner et al.

(10) Patent No.: US 7,485,642 B2
(45) Date of Patent: Feb. 3, 2009

(54) METHOD FOR TREATING SEPTIC SHOCK

(75) Inventors: Anders Oldner, Sollentuna (SE); Michael Wanecek, Lidingö (SE); Eddie Weitzberg, Stockholm (SE); Anders Rudehill, Bromma (SE)

(73) Assignee: Orion Corporation, Espoo (FI)

( * ) Notice: Subject to any disclaimer, the term of this patent is extended or adjusted under 35 U.S.C. 154(b) by 255 days.

(21) Appl. No.: 10/312,450

(22) PCT Filed: Jun. 28, 2001

(86) PCT No.: PCT/FI01/00614

§ 371 (c)(1),
(2), (4) Date: Mar. 24, 2003

(87) PCT Pub. No.: WO02/00220

PCT Pub. Date: Jan. 3, 2002

(65) Prior Publication Data

US 2003/0158201 A1 Aug. 21, 2003

(30) Foreign Application Priority Data

Jun. 29, 2000 (FI) .................................. 20001542

(51) Int. Cl.
*A61K 31/50* (2006.01)
(52) U.S. Cl. ....................... 514/247; 514/921
(58) Field of Classification Search ................. 514/247, 514/921

See application file for complete search history.

(56) References Cited

FOREIGN PATENT DOCUMENTS

| EP | 0565546 | 10/1993 |
|---|---|---|
| WO | WO 93/21921 | 11/1993 |
| WO | WO 99/66912 | 12/1999 |
| WO | WO 01/00211 | 1/2001 |

OTHER PUBLICATIONS

Spitzer et al. Prog Clin Biol Res. 1987; 236A, pp.573-590.*
Paul S. Pagel et al., "Influence of Levosemendan, Pimobendan, and Milrinone on the Regional Distribution of Cardiac Output in Anaesthetized Dogs.", British Journal of Pharmacology, vol. 119, pp. 609-615, 1996.
Ferenc Folláth et al., "Dose-Ranging and Safety with Intravenous Levosimendan in Low-Output Heart Failure: Experience in Three Pilot Studies and Outline of the Levosimendan Infusion Versus Dobutamine (LIDO) Trial.", Am J Cardiol, vol. 83, pp. 21-25, 1999.
Athur P. Wheeler et al., "Treating Patients with Severe Sepsis", The New England Journal of Medicine, vol. 340, pp. 207-214, Jan. 1999.
Matejovic et al., "Successful reversal of resistent hypodynamic septic shock with levosimendan," Acta Anaesthesiol. Scand. 49:127 (2005).
Powell B. P. et al. "Levosimendan in septic shock: a case series," *Br. J. Anaesthesia* (2007) 99(3):447.
Press Release: "Abbott Reports Improved Clinical Course with Levosimendan (Simdax®) When Added to Standard Therapy in Acute Decompensated Heart Failure Trial" (2007).

* cited by examiner

*Primary Examiner*—Sreeni Padmanabhan
*Assistant Examiner*—Shobha Kantamneni
(74) *Attorney, Agent, or Firm*—Finnegan, Henderson, Farabow, Garrett & Dunner, LLP

(57) ABSTRACT

Levosimendan, or (−)-[[4-(1,4,5,6-tetrahydro-4-methyl-6-oxo-3-pyridazinyl)phenyl]hydrazono]propanedinitrile, which has been mentioned for the treatment of congestive heart failure, is useful in the treatment of septic shock.

8 Claims, 4 Drawing Sheets

METHOD FOR TREATING SEPTIC SHOCK

This application is a national stage filing of PCT International Application No. PCT/FI01/00614, filed on Jun. 28, 2001. This application also claims the benefit of priority under 35 U.S.C. § 119(a) to Finnish patent application no. 20001542, filed on Jun. 29, 2000.

TECHNICAL FIELD

The present invention relates to a method for the treatment of septic shock by administering levosimendan, or (−)-[[4-(1,4,5,6-tetrahydro-4-methyl-6-oxo-3-pyridazinyl)phenyl]hydrazono]propanedinitrile (I), or pharmaceutically acceptable salts thereof, to a patient in need of such treatment.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure and has significant calcium dependent binding to troponin. Levosimendan is represented by the formula:

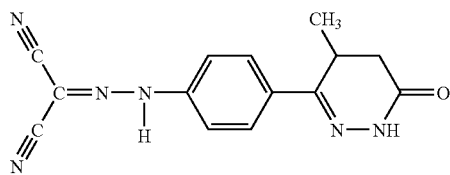

I

The hemodynamic effects of levosimendan in man are described in Sundberg, S. et al., Am. J. Cardiol., 1995; 75: 1061-1066 and in Lilleberg, J. et al., J. Cardiovasc. Pharmacol., 26(Suppl.1), S63-S69, 1995. Pharmacokinetics of levosimendan in man after i.v. and oral dosing is described in Sandell, E.-P. et al., J. Cardiovasc. Pharmacol., 26(Suppl.1), S57-S62, 1995. The use of levosimendan in the treatment of myocardial ischemia is described in WO 93/21921. The use of levosimendan in the treatment of pulmonary hypertension is described in WO 99/66912. Clinical studies have confirmed the beneficial effects of levosimendan in heart failure patients.

Septic shock (also known as sepsis) is the leading cause of morbidity and mortality in the intensive care units. Despite increased knowledge about the pathophysiology underlying the clinical symptoms mortality remains high and has not decreased substantially over the last decades.

There are several causes of septic shock including bacterial, fungal and viral infections as well as non-invasive stimuli such as multiple trauma, severe burns, organ transplantations and pancreatitis. The fatal outcome of septic shock has recently been linked to the systemic release of substantial amounts of various cytokines in the body.

Septic shock requires prompt treatment since the patient's condition often deteriorates rapidly. Symptoms of septic shock include fever, hypothermia, falling blood pressure, rapid breathing, rapid heartbeat, skin lesions and leakage of plasma proteins into the tissues, metabolic acidosis and elevated plasma lactate. Septic shock is particularly characterised by maldistribution of blood flow and disturbances in tissue oxygen in various organs of the body. Distribution of blood flow may become heterogenous with subsequent under- and overperfusion of various tissues. These disturbances have been noted both at the macro- as well as at the microcirculatory level. Septic patient usually die as a result of poor tissue perfusion and injury followed by multiple organ failure.

One of the organs in which the disturbances in nutritive flow is especially important is the gut. The importance of preserved of splanchnic blood flow in various shock conditions, including septic shock, has been largely emphasized in the literature. Reductions in splanchnic blood flow have been a suggested contributor to the development of multiple organ failure as well as maintenance of sepsis by translocation of gut derived bacteria over a hyperpermeable gut wall.

Current therapeutic strategies in sepsis include antibiotics, in certain cases surgical intervention, blood volume replacement as well as inotropic support to the failing circulation. However, the current therapy has not proven to be successful. Insufficient response to intropic drugs in terms of cardiac output is not uncommon. Also the distribution of blood flow to various organs may become negatively affected. For example, splanchnic blood flow is not increased in spite of increased cardiac output. Thus, an improved method for treating septic shock would be of great value.

SUMMARY OF THE INVENTION

It has now been found that in the porcine model of endotoxin shock levosimendan unexpectedly counteracts endotoxin-induced splanchnic hyperperfusion as well as endotoxin-induced decreases in cardiac output. These favourable effects suggest that levosimendan is particularly beneficial in the treatment of septic shock.

Therefore, the present invention provides the use of (−)-[[4-(1,4,5,6-tetra-hydro-4-methyl-6-oxo-3-pyridazinyl)phenyl]hydrazono]propanedinitrile or a pharmaceutically acceptable salt thereof in the manufacture of a medicament for the treatment septic shock.

The present invention also provides a method for the treatment of septic shock in a patient, said method comprising administering to a patient in need thereof an effective amount of (−)-[[4-(1,4,5,6-tetrahydro-4-methyl-6-oxo-3-pyridazinyl)-phenyl]hydrazono]propanedinitrile or a pharmaceutically acceptable salt thereof.

DETAILED DESCRIPTION

Figure 1:
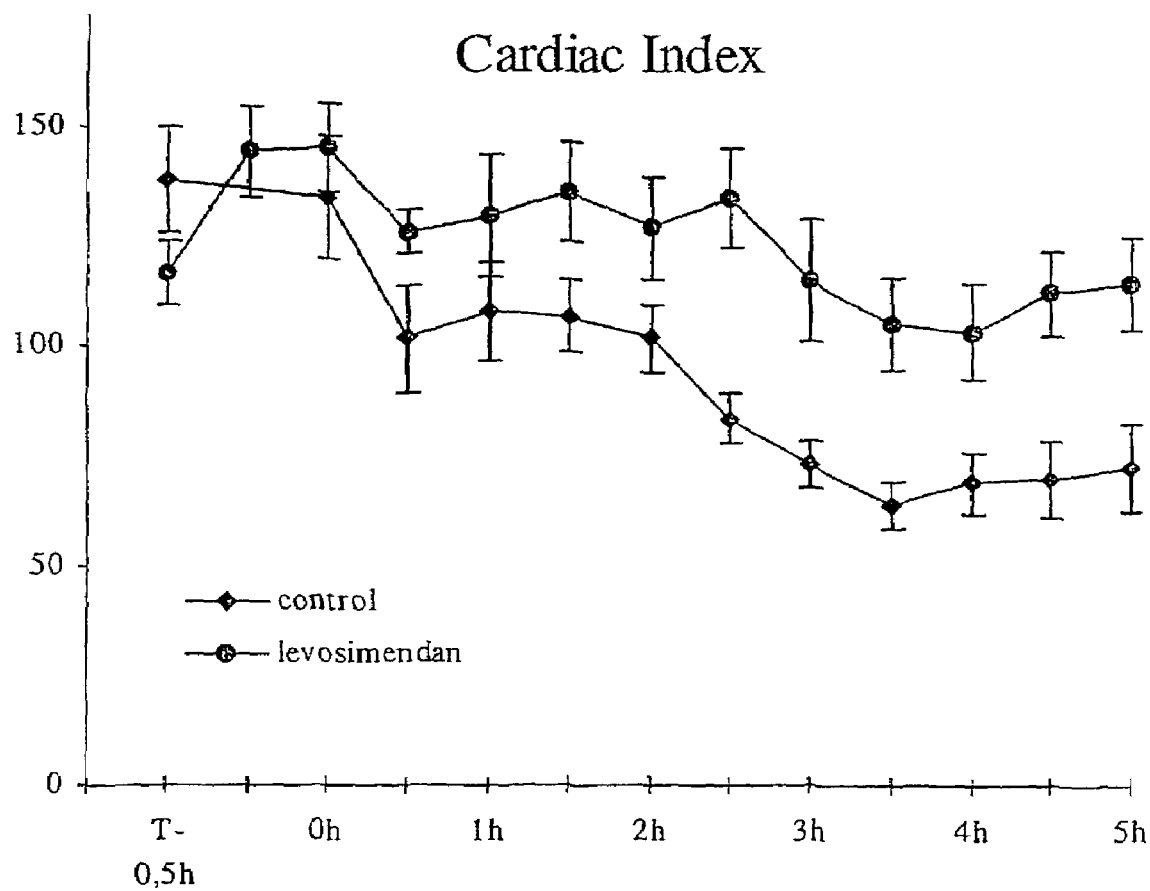
FIG. 1 shows the effect of levosimendan on the cardiac index in a porcine model of endotoxin shock compared to control.

The method of the invention comprises a step of administering to a subject an amount of levosimendan effective to reduce, inhibit or prevent symptoms of septic shock in a patient. In particular the method comprises administering to a patient an amount of levosimendan effective to counteract endotoxin-induced harmful effects on the peripheral circulation of a patient. The term "treatment of septic shock" is intended to cover therapeutic and/or prophylactic treatments. The administration of levosimendan can be enteral, e.g. oral or rectal, or parenteral, e.g. intravenous or transdermal.

The effective amount of levosimendan to be administered to a subject depends upon the condition to be treated, the route of administration, age, weight and the condition of the patient. In general levosimendan is administered orally to man in daily dose from about 0.1 to 20 mg, preferably from 0.2 to 15 mg, more preferably from 0.5 to 10 mg, given once a day or divided into several doses a day, depending on the age, body weight and condition of the patient. Levosimendan can be administered by intravenous infusion using the infusion rate typically from about 0.01 to 10 µg/kg/min, more typically from about 0.02 to 5 µg/kg/min. For the intravenous treatment of septic shock an intravenous bolus of 10-200 µg/kg followed by infusion of 0.2-3 µg/kg/min may be needed.

Levosimendan is formulated into dosage forms suitable for the treatment of septic shock using the principles known in the art. It is given to a patient as such or preferably in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

For oral administration in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. For controlled release oral compositions release controlling components can be used. Typical release controlling components include hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Typically a tablet or a capsule comprises from about 0.1 to 10 mg, more typically 0.2 to 5 mg, of levosimendan.

Formulations suitable for intravenous administration such as injection or infusion formulation, comprise sterile isotonic solutions of levosimendan and vehicle, preferably aqueous solutions. Typically an intravenous infusion solution comprises from about 0.01 to 0.1 mg/ml of levosimendan.

Salts of levosimendan may be prepared by known methods. Pharmaceutically acceptable salts are useful as active medicaments, however, preferred salts are the salts with alkali or alkaline earth metals.

EXAMPLES

Pharmaceutical Example

| Hard gelatin capsule size 3 | |
| --- | --- |
| Levosimendan | 2.0 mg |
| Lactose | 198 mg |

The pharmaceutical preparation in the form of a capsule was prepared by mixing levosimendan with lactose and placing the powdery mixture in hard gelatin capsule.

Experiments 20 kg landrace pigs were anesthetized and catheterized. After baseline measurements 8 pigs received 200 µg/kg levosimendan as a 10 minute bolus followed by an infusion of 200 µg/kg/hour. 9 animals served as controls.

In the second phase of the experiment the animals were given an infusion of endotoxin (from *E. Coli* bacteria) 30 minutes after the start of the bolus dose of levosimendan. The endotoxin infusion was maintained for 3 hours and the levosimendan infusion was maintained throughout the experiment until 5 hours after onset of endoxemia. Comparison between the two groups was made with ANOVA.

Figure 2:
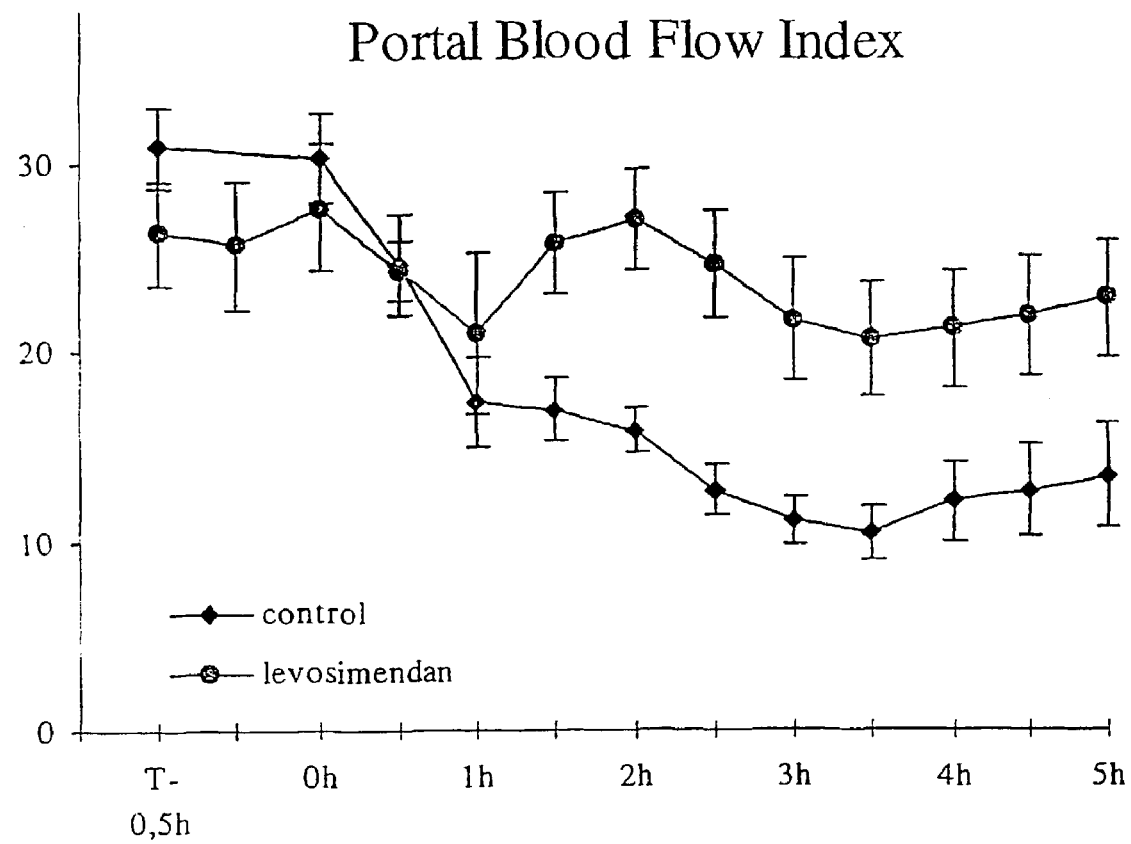
FIG. 2 shows the effect of levosimendan on the portal blood flow index in a porcine model of endotoxin shock compared to control.
Figure 3:
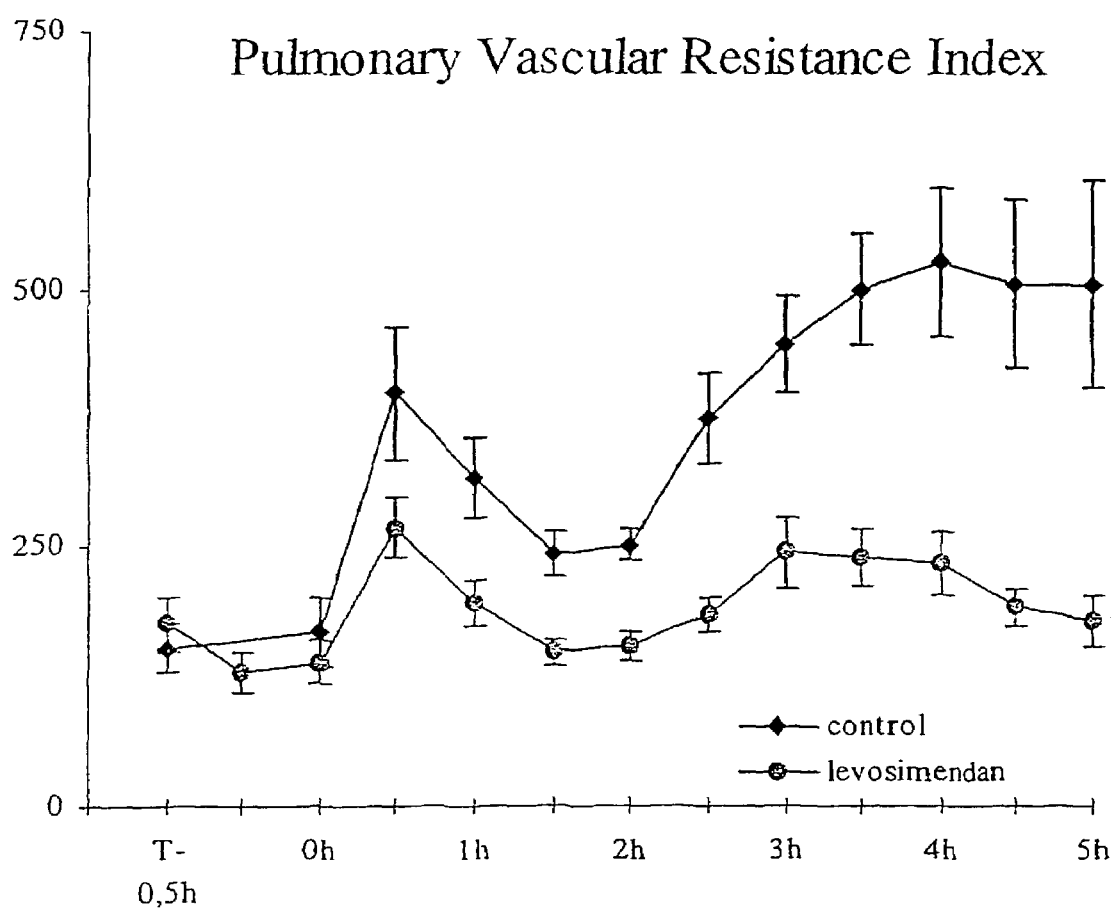
FIG. 3 shows the effect of levosimendan on the pulmonary vascular resistance index in a porcine model of endotoxin shock compared to control.
Figure 4:
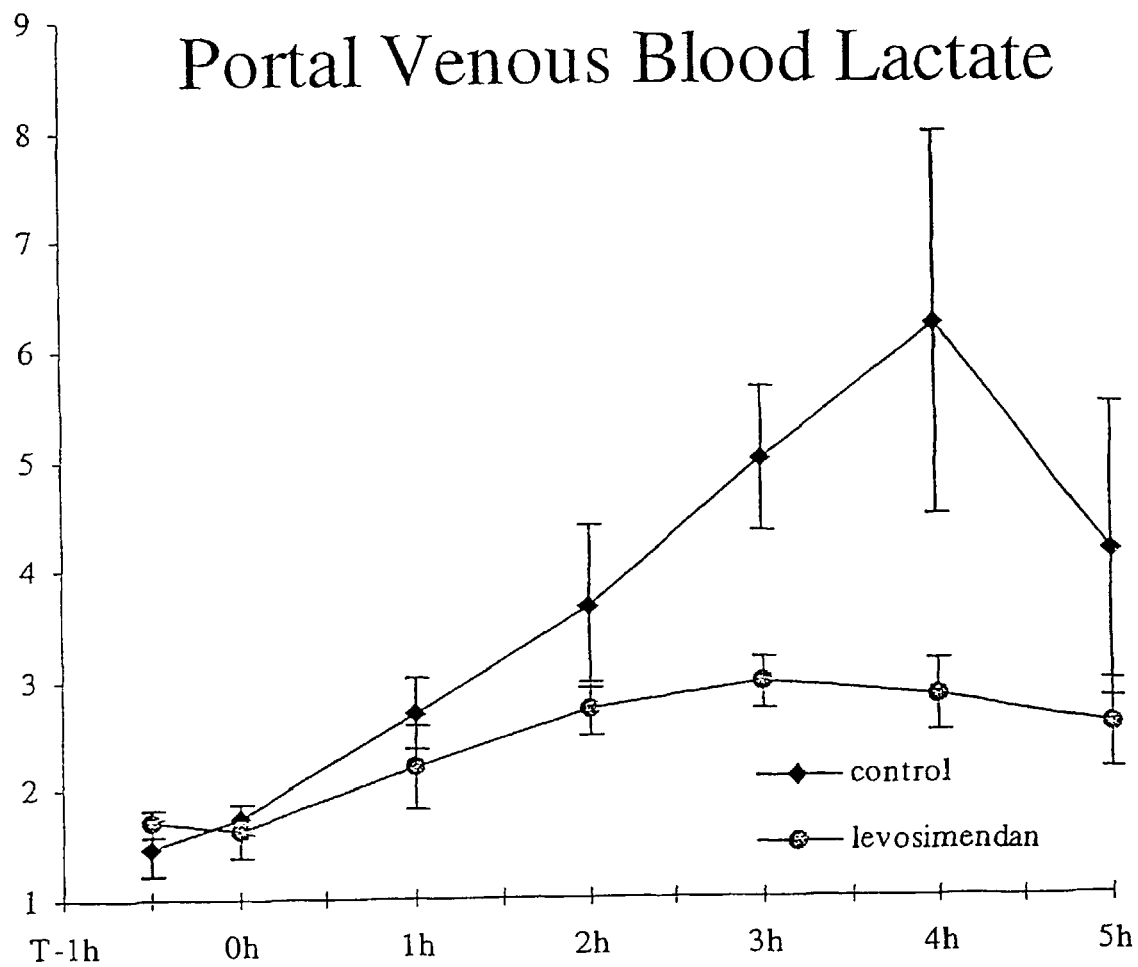
FIG. 4 shows the effect of levosimendan on the portal venous blood flow lactate in a porcine model of endotoxin shock compared to control.

The changes in the cardiac index, splanchnic (portal) blood flow index, portal venous blood lactate and pulmonary vascular resistance are shown in FIGS. 1-4. In the Figures, (−0.5 h) means the start of levosimendan bolus and (0 h) the start of endotoxin infusion. The results show that levosimendan can significantly counteract endotoxin-induced circulatory disorders. All levosimendan treated animals survived whereas one animal in the control group died.

The invention claimed is:

1. A method for the treatment of septic shock in a patient, said method comprising administering to a patient in need thereof an effective amount of (−)-[[4-(1,4,5,6-tetrahydro-4-methyl-6-oxo-3-pyridazinyl)phenyl]-hydrazono]propanedinitrile or a pharmaceutically acceptable salt thereof.

2. A method according to claim 1, wherein an intravenous bolus of 10-200 µg/kg followed by infusion of 0.2-3 µg/kg/min of (−)-[[4-(1,4,5,6-tetrahydro-4-methyl-6-oxo-3-pyridazinyl)phenyl]hydrazono]propanedinitrile is administered.

3. A method according to claim 1, which comprises administering the (−)-[[4-(1,4,5,6-tetrahydro-4-methyl-6-oxo-3-pyridazinyl)phenyl]-hydrazono]propanedinitrile, or pharmaceutically acceptable salt thereof, in the form of a solution.

4. A method according to claim 1, which comprises administering the (−)-[[4-(1,4,5,6-tetrahydro-4-methyl-6-oxo-3-pyridazinyl)phenyl]-hydrazono]propanedinitrile, or pharmaceutically acceptable salt thereof, in the form of an intravenous solution.

5. A method according to claim 1, which comprises administering (−)-[[4-(1,4,5,6-tetrahydro-4-methyl-6-oxo-3-pyridazinyl)phenyl]-hydrazono]propanedinitrile.

6. A method according to claim 1, which comprises administering a pharmaceutically acceptable salt of (−)-[[4-(1,4,5,6-tetrahydro-4-methyl-6-oxo-3-pyridazinyl)phenyl]-hydrazono]propanedinitrile.

7. A method according to claim 6, wherein the salt is an alkali or alkaline earth metal salt.

8. A method for increasing splanchnic blood flow in a patient suffering from septic shock comprising administering to a patient in need thereof an effective amount of (−)-[[4-(1,4,5,6-tetrahydro-4-methyl-6-oxo-3-pyridazinyl)phenyl]-hydrazono]propanedinitrile, or a pharmaceutically acceptable salt thereof.

* * * * *